Figure 1:
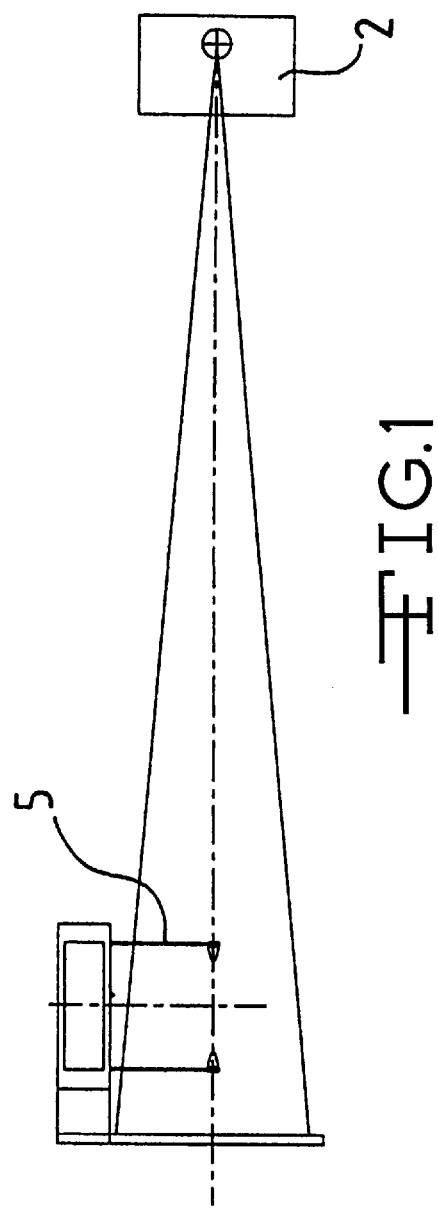

United States Patent
Suuronen

[11] Patent Number: 5,841,834
[45] Date of Patent: Nov. 24, 1998

[54] FILTER ARRANGEMENT IN A RADIOGRAPHY APPARATUS

[75] Inventor: Esa Pekka Suuronen, Espoo, Finland

[73] Assignee: Orion-Yhtyma OY, Helsinki, Finland

[21] Appl. No.: 693,166

[22] PCT Filed: Feb. 14, 1995

[86] PCT No.: PCT/FI95/00069

§ 371 Date: Nov. 29, 1996

§ 102(e) Date: Nov. 29, 1996

[87] PCT Pub. No.: WO95/21571

PCT Pub. Date: Aug. 17, 1995

[30] Foreign Application Priority Data

Feb. 15, 1994 [FI] Finland .................................. 940707

[51] Int. Cl.$^6$ .................................................. A61B 6/08
[52] U.S. Cl. ........................................ 378/156; 378/206
[58] Field of Search ................................. 378/156, 158, 378/159, 168, 170, 177, 204, 205, 206, 38, 162, 163, 165, 166

[56] References Cited

U.S. PATENT DOCUMENTS

| | | |
|---|---|---|
| 3,708,663 | 1/1973 | Biederman ............................. 378/206 |
| 3,947,689 | 3/1976 | Wagner ............................... 378/206 X |
| 4,223,228 | 9/1980 | Kaplan . |
| 4,355,230 | 10/1982 | Wilson et al. ...................... 378/207 X |
| 4,429,409 | 1/1984 | Barry et al. ................................ 378/45 |
| 4,521,112 | 6/1985 | Kuwabara et al. . |
| 4,618,980 | 10/1986 | Lescrenier et al. . |
| 4,670,896 | 6/1987 | Klausz ............................... 378/206 X |
| 4,744,099 | 5/1988 | Huettenrauch et al. . |
| 4,947,090 | 8/1990 | Armond et al. . |
| 5,195,115 | 3/1993 | Schiller et al. ..................... 378/158 X |
| 5,200,986 | 4/1993 | Schlie . |
| 5,278,887 | 1/1994 | Chiu et al. . |

*Primary Examiner*—David P. Porta
*Attorney, Agent, or Firm*—Hodgson, Russ, Andrews, Woods & Goodyear LLP

[57] ABSTRACT

A filter arrangement in a radiography apparatus in order to define the intensity of the radiation beam incident upon the object. To the movable filter part in front of the radiation source (2) there is coupled an electric circuit element, for example a potentiometer, from which the signal is applied further to a row (8) of light-emitting diodes in the vicinity of the object to be radiographed, for example the patient's head (7). When the filter is moved, the electric signal controls the light-emitting diodes so that the light-emitting diodes which become illuminated in the row will indicate the boundary of the filtered radiation beam at a given time.

9 Claims, 5 Drawing Sheets

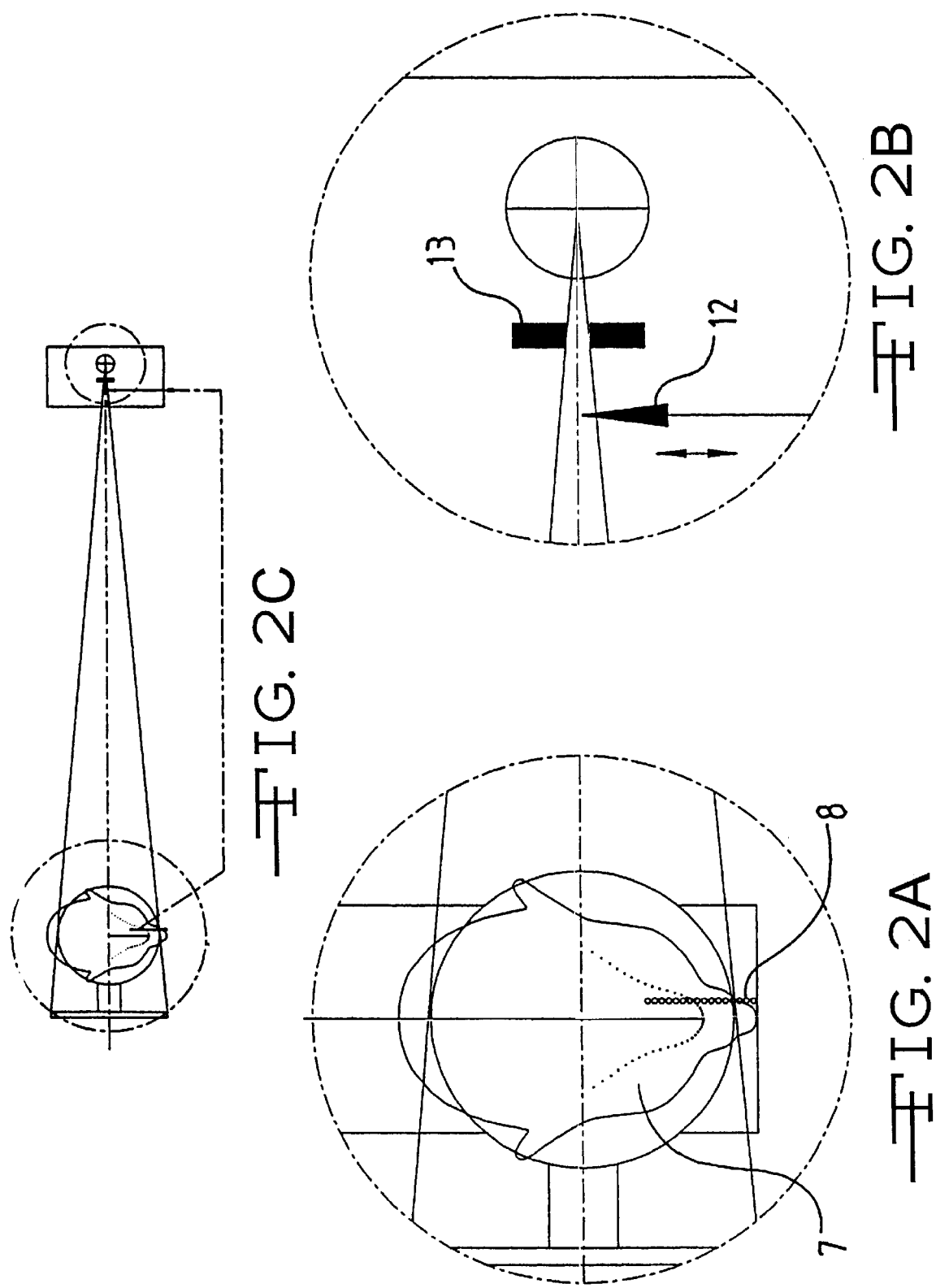

FILTER ARRANGEMENT IN A RADIOGRAPHY APPARATUS

The present invention relates to a filter arrangement in a radiography apparatus to define the intensity of the radiation beam incident upon the patient, the radiography apparatus incorporating an X-ray source, a movable filter placed in front of it, and means for supporting the patient in order to keep the object to be radiographed immobile relative to the X-ray beam, there being in alignment with the patient light-emitting means to indicate the dimension of the filtered radiation beam at a given time, and there being between the said light-emitting means and the filter-moving means a signal communication to implement the positional dependency between them.

In radiography it is in general important to define suitably the shape and intensity of the beam of rays relative to the object to be radiographed, in order not to subject the patient to unnecessary radiation and also otherwise in order to obtain an image exposed with maximal expediency. For example, in cefalometry, the patient's head, or parts of the skull, is recorded as seen from the side, in which case it is often expedient to filter more that side of the beam of rays which is incident upon the patient's face, whereupon the outline of the patient's face will be visible in the X-ray image produced. This is, in a known manner, achieved by means of a wedge-shaped filter placed between the source of radiation and the object to be radiographed, the filter being in general arranged so as to be movable in a plane perpendicular to the main axis of the radiation beam so that the thinner edge of the wedge is closer to the main axis of the beam.

In the positioning of the wedge-shaped filter of the radiation beam it is, of course, important to know to which point in the patient at a given location of the filter the filtering effect extends. In said cefalometry it is prior known, for example, to measure, by using the means for supporting the patient's head, certain important dimensions and to position the filter on the basis of these, either manually or automatically by using a motor. A system of this type is disclosed, for example, in FI patent 68515.

A slightly different known method, resembling this, is one in which a movable light-emitter is arranged in the vicinity of the means for supporting the patient's head, the emitter emitting a beam of light indicating the boundary of the radiation beam filtered by the wedge filter. The technical implementation is such that from the means for moving the light-emitter there departs an electric signal to the filter motor, which then drives the filter to the correct position.

In adjusting the filtering of the ratiation beam is would, however, be desirable to work at a distance from the patient and not in the immediate vicinity of the patient positioned in place by using the head-supporting means, as in the cases described above. Furthermore, the transfer of the filter by using a motor, of course, makes the structure more complicated and increases its price. It is therefore an object of the present invention to provide a reliably functioning arrangement which is, nevertheless, relatively simple in its implementation.

To achieve this object, the invention is characterized in that to the filter-moving means there are coupled circuit means which create an electric signal dependent on the position of the moving means, there being further arranged a signal communication from the circuit means to light emitters which are fitted in the vicinity of the object to be radiographed and are arranged in a row so that, according to the position of the filter-moving means, a certain light emitter or a plurality of light emitters will become illuminated to indicate the boundary of the filtered radiation beam.

Compared with known methods, the principle in the present invention is thus the opposite: the light emitters serve to indicate to the operator the boundary of the filtered radiation beam produced by the filter wedge. In other words, when the operator moves the filter, a signal proportional to the filter position is applied to a light-emitting diode row arranged, for example, above the patient, whereupon the number of illuminated light-emitting diodes, or a light-emitting diode at a certain point, will indicate the boundary of the filtered radiation beam. The advantage of this opposite operating principle is thus the ability to function without an expensive motor.

Figure 3B:
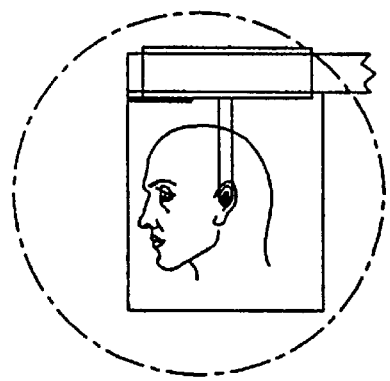
Figure 3A:
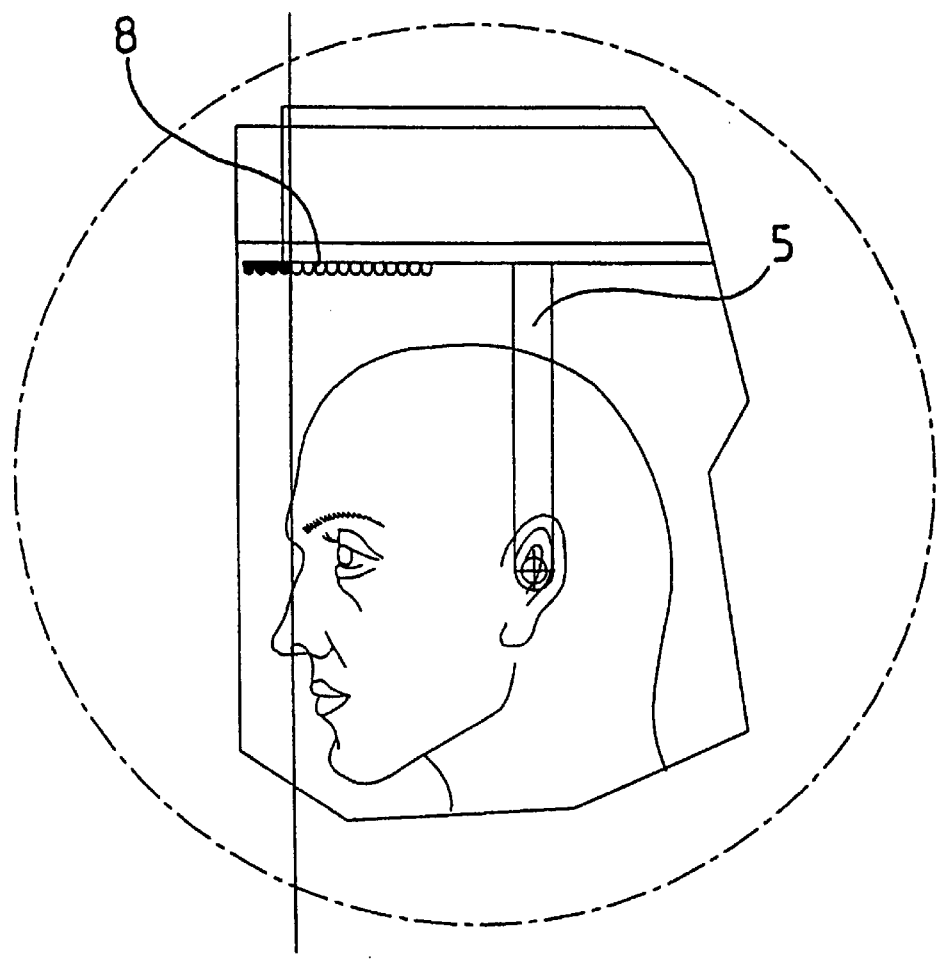
Figure 4:
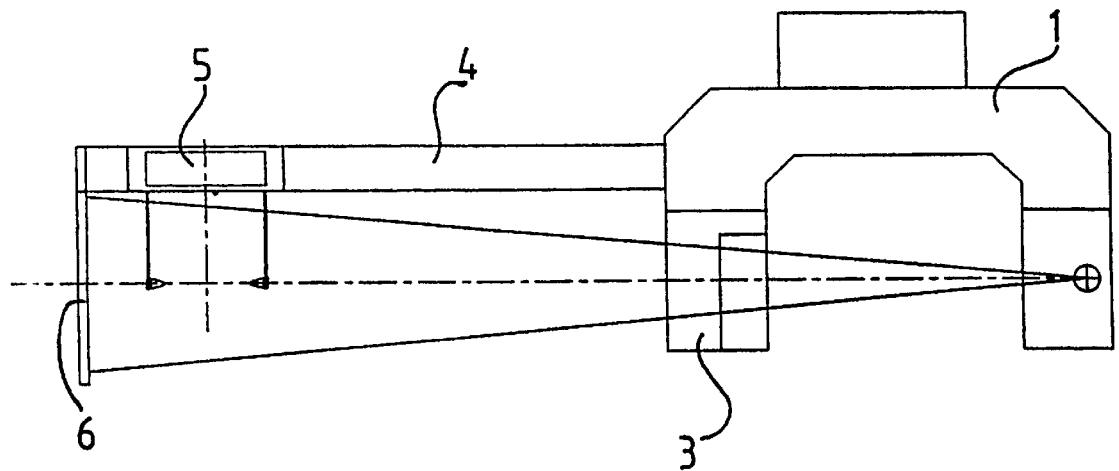
Figure 5:
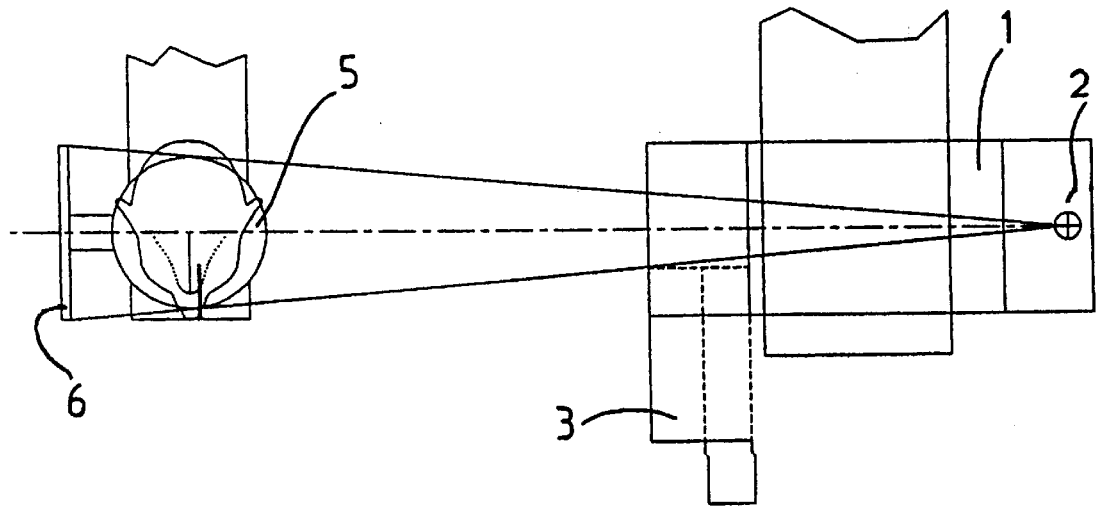
Figure 6:
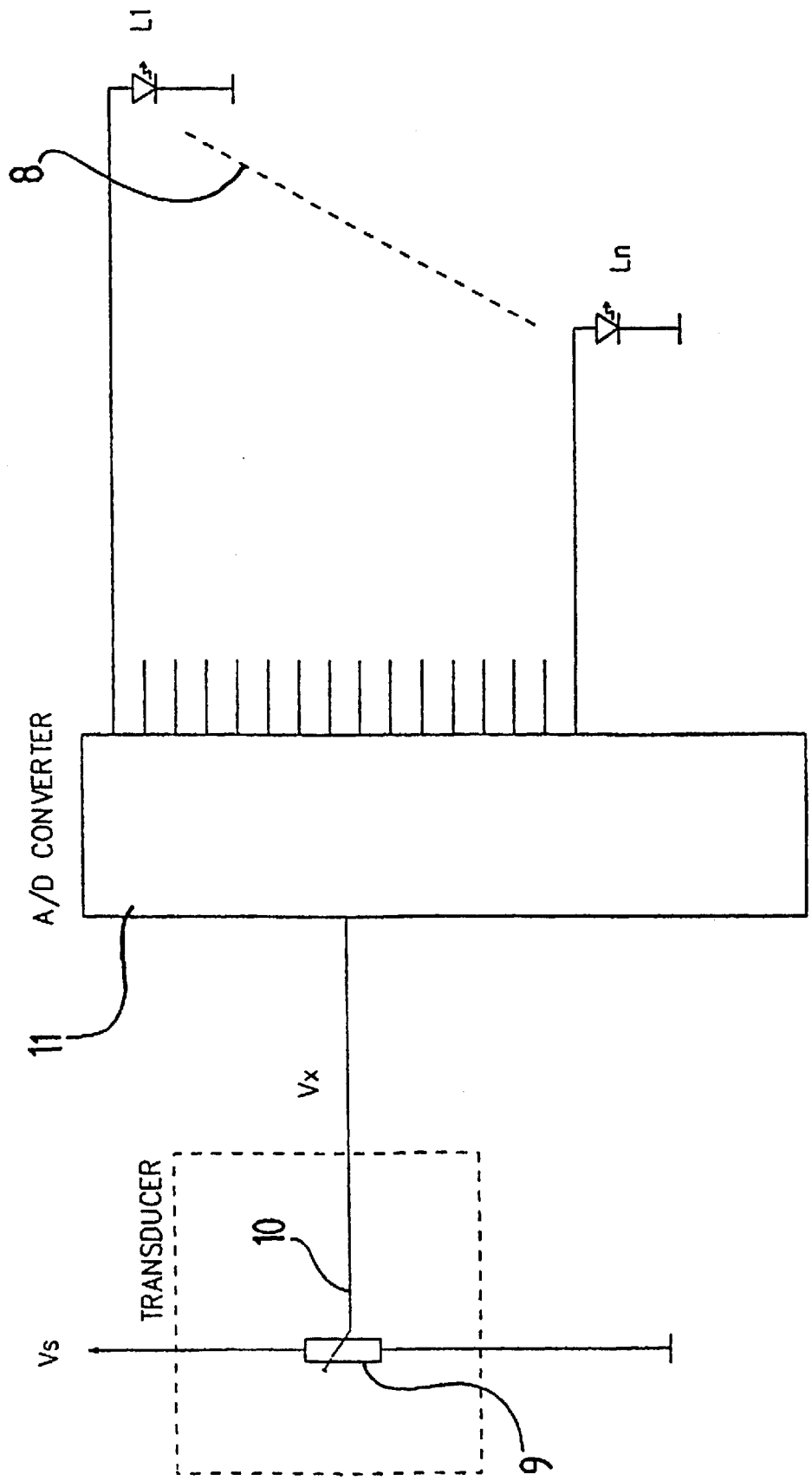

The invention and its other characteristics are described below in greater detail in the form of an example and with reference to the accompanying drawings, wherein FIG. 1 depicts diagrammatically an arrangement having a radiation source and means for supporting the patient, FIG. 2 depicts a top view of the same, in such a manner that also the patient's head is shown, FIG. 3 depicts the patient's head and the head-supporting means, FIG. 4 depicts diagrammatically a combination of a panoramic apparatus and a cefalostat, FIG. 5 depicts a top view of the system of FIG. 4, and FIG. 6 depicts one implementation of the signal path in accordance with the invention.

In FIGS. 1–6, reference numeral 2 indicates the radiation source; 5 the means for supporting the patient's head; 7 the object to be radiographed; 8 the light-emitting diode row, to be described below; 12 the movable wedge filter; and 13 the shutter defining the radiation beam.

FIGS. 4 and 5 depict an example of how equipment intended for cefalostatic imaging is linked to a conventional panoramic radiography apparatus. More precisely, reference numeral 1 indicates the so-called support arm of a panoramic radiography apparatus, the arm having at one end a radiation source 2 and at the opposite end an X-ray film casette with the necessary transfer mechanism 3. In this context it is hardly necessary to describe the panoramic radiography apparatus, well known to an expert in the art. In the embodiment depicted, a projection 4 has been added to the panoramic apparatus, there being, at the end of the projection, head-supporting means 5 and, behind them, the cassette holder 6 of the cefalostat. When the X-ray source 2 of the panoramic apparatus is used for cefalostatic imaging, the moving film cassette mechanism 3 is transferred aside, out of the way of the radiation beam.

In accordance with the present invention, a transducer producing an electric signal is coupled to the moving part of the filter, for example, a moving tap of a slide potentiometer, as shown in FIG. 6. A signal corresponding to the position of the tap of the slide potentiometer is applied to an A/D converter 11, from where control signals are further applied to light-emitting diodes 8 arranged in a row above the patient. The control is either such that precisely the light-emitting diode corresponding to the position of the potentiometer becomes illuminated, or all of the light-emitting diodes on one side of the position become illuminated, as is shown, for example, in FIG. 3. In this case the light-emitting diodes which have become illuminated at the same time illustrate the dimension of the filtered area.

It is clear that there are also other methods of producing an electric signal corresponding to the filter-moving means, the signal then being used for controlling a row 8 of light emitters. The potentiometer may, of course, be a slide potentiometer as shown in the figures, but it may just as well be a multi-turn rotary potentiometer, which is, for example, directly coupled to the control screw serving as the filter-moving means. Furthermore, the electric control signal may be produced by an optical transducer or Hall transducer coupled to the filter-moving means by methods evident to an expert in the art. The circuit means may, for example, include a voltage/frequency converter and a pulse counter, which convert an analog voltage signal to a suitable digital control signal.

I claim:

1. A filter arrangement in a radiography apparatus in order to filter the radiation beam incident upon a patient, the radiography apparatus incorporating a source of X ray radiation (2), a movable filter placed in front of the source, means (5) for supporting the patient in order to keep an object (7) to be radiographed immobile relative to the beam of X-rays, and there being in alignment with the patient light-emitting means (8) to indicate a dimension of the filtered portion of the radiation beam at a given time, and there being a signal communication between the said light-emitting means (8) and the movable filter in order to effect a positional dependency between them, characterized in that to the movable filter there are coupled circuit means (9–11) producing an electric signal dependent on the position of the filter, there being provided for the circuit means a further signal communication to light emitting means (8) arranged in a row, fitted in the vicinity of the object to be imaged, in such a manner that a certain light emitter or certain light emitters will become illuminated according to the position of the movable filter to indicate the boundary of the filtered radiation beam.

2. A filter arrangement according to claim 1, characterized in that the circuit means are made up of a slide potentiometer (9) a movable part (10) of which is mechanically coupled to the filter.

3. A filter arrangement according to claim 1, characterized in that the circuit means are made up of an optical transducer.

4. A filter arrangement according to claim 1, characterized in that the circuit means are made up of a Hall transducer.

5. A filter arrangement according to claim 1, characterized in that the light emitting means (8) are light-emitting diodes.

6. A filter arrangement according to claim 5, characterized in that the light-emitting diodes (8) are light-emitting diode pieces placed in a straight row.

7. A filter arrangement according to claim 1, characterized in that the light emitting means (8) are arranged in a vertical plane which runs through the center line of the object to be radiographed in a suitable frame part above the object to be radiographed (7).

8. A filter arrangement according to claim 1, characterized in that the circuit means include an A/D converter (11) for converting an analog signal corresponding to the filter position to a digital signal to control the light emitting means.

9. A filter arrangement according to claim 1, characterized in that the circuit means include a voltage/frequency converter and a pulse counter to convert a location signal obtained from a measuring transducer to a control signal to control the light emitting means.

* * * * *